United States Patent [19]

Hasegawa et al.

[11] 4,302,467
[45] Nov. 24, 1981

[54] ANTIBACTERIAL AND ANTIFUNGAL COMPOSITION

[75] Inventors: Masayasu Hasegawa, Kyoto; Hideo Nishikawa, Ibaraki; Yasuo Kotani, Hirakata, all of Japan

[73] Assignee: Nippon Gohsei Kagaku Kogyo Kabushiki Kaisha, Osaka, Japan

[21] Appl. No.: 151,652

[22] Filed: May 20, 1980

Related U.S. Application Data

[62] Division of Ser. No. 58,448, Jul. 18, 1979, Pat. No. 4,242,356.

[30] Foreign Application Priority Data

Dec. 26, 1978 [JP] Japan ............................... 53/161816
Dec. 26, 1978 [JP] Japan ............................... 53/161817
Dec. 26, 1978 [JP] Japan ............................... 53/161818
Dec. 26, 1978 [JP] Japan ............................... 53/161819
Dec. 26, 1978 [JP] Japan ............................... 53/161820
Dec. 26, 1978 [JP] Japan ............................... 53/161821
Dec. 26, 1978 [JP] Japan ............................... 53/161822

[51] Int. Cl.$^3$ ..................... A01N 37/06; A01N 37/34; A01N 43/36; A01N 43/78
[52] U.S. Cl. .................................. 424/270; 424/314
[58] Field of Search ................... 424/314, 270

[56] References Cited

PUBLICATIONS

The Merck Index 9th Ed. (1976) pp. 135, 279, 375, 644, 950, 994, 1126, 1184, 1197, 1198.
Kuehle et al.; C. A. vol. 62 No. 4 3973 (1965).

Primary Examiner—Allen J. Robinson
Attorney, Agent, or Firm—Armstrong, Nikaido, Marmelstein & Kubovcik

[57] ABSTRACT

An antibacterial and antifungal composition comprising (A) at least one member selected from the group consisting of dehydroacetic acid, sorbic acid and their alkali metal salts and (B) at least one member selected from the group consisting of o-phenylphenol and its alkali metal salts, p-chloro-m-xylenol, 2-(4-thiazolyl)-1H-benzimidazole, 8-hydroxyquinoline and its salts and chelates, methyl 1-(butylcarbamoyl)-2-benzimidazolecarbamate, tetrachloroisophthalonitrile and N-(fluorodichloromethylthio)phthalimide. The antibacterial and antifungal effects can be synergistically increased when the component (A) is employed in combination with the component (B).

1 Claim, No Drawings

ANTIBACTERIAL AND ANTIFUNGAL COMPOSITION

This is a division of application Ser. No. 58,448, filed July 8, 1979, now U.S. Pat. No. 4,242,356 issued Dec. 30, 1980.

BACKGROUND OF THE INVENTION

The present invention relates to a composition useful as antibacterial and antifungal agent, and more particularly to a composition mainly containing dehydroacetic acid, sorbic acid or their alkali metal salts.

It is well known that dehydroacetic acid, sorbic acid and their alkali metal salts are useful as antibacterial and antifungal agents. The toxicity of these antibacterial and antifungal agents is so low that their addition to foods is permitted, and they are agents of very high safety. Therefore, if these agents are usable in any fields such as general industrial products and agricultural products, to say nothing of foods, the usefulness of these agents becomes very great. However, the antibacterial and antifungal effects thereof are not always satisfactory, and they are restricted in the application to industrial products such as paints, sizing agents and adhesives.

SUMMARY OF THE INVENTION

In accordance with the present invention, there is provided an antibacterial and antifungal composition comprising (A) at least one member selected from the group consisting of dehydroacetic acid, sorbic acid and their alkali metal salts and (B) at least one member selected from the group consisting of o-phenylphenol and its alkali metal salts, p-chloro-m-xylenol, 2-(4-thiazolyl)-1H-benzimidazole, 8-hydroxyquinoline and its salts and chelates, methyl 1-(butylcarbamoyl)-2-benzimidazolecarbamate, tetrachloroisophthalonitrile and N-(fluorodichloromethylthio)phthalimide. The synergistic effect on the antibacterial and antifungal properties is very remarkable, when the component (A) is employed in combination with the component (B), and the composition of the invention can be availably employed as antibacterial and antifungal agents in various industrial products and agricultural products.

DETAILED DESCRIPTION

There are employed, as the component (A) of the composition of the invention, dehydroacetic acid, sorbic acid and their alkali metal salts such as sodium dehydroacetate, potassium dehydroacetate, sodium sorbate and potassium sorbate. These compounds may be employed alone or in admixture thereof.

Examples of a compound employed as the component (B) of the composition of the invention are o-phenylphenol and its alkali metal salts shown by the following formula:

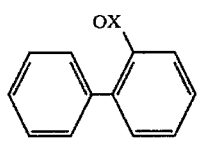

wherein X is hydrogen or an alkali metal, p-chloro-m-xylenol shown by the following formula:

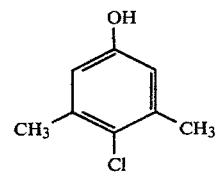

2-(4-thiazolyl)-1H-benzimidazole shown by the following formula:

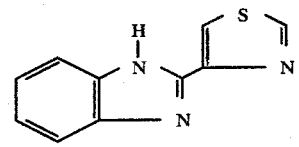

8-hydroxyquinoline shown by the following formula:

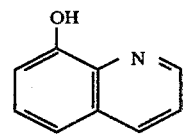

salts of 8-hydroxyquinoline with organic or inorganic acids such as hydrochloric acid, sulfuric acid and acetic acid, e.g. 8-hydroxyquinoline sulfate of the formula:

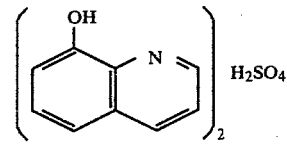

chelates of 8-hydroxyquinoline with metals such as copper and zinc, methyl 1-(butylcarbamoyl)-2-benzimidazolecarbamate shown by the following formula:

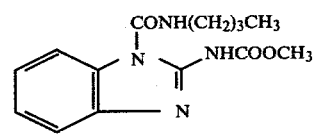

tetrachloroisophthalonitrile shown by the following formula:

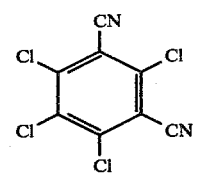

and N-(fluorodichloromethylthio)phthalimide shown by the following formula:

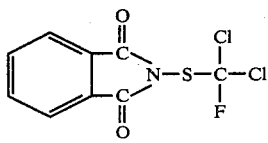

These compounds may be employed anone or in admixture thereof.

The components (A) and (B) may be employed in any proportions. In general, it is desirable to employ the component (B) in an amount of 1% to 40% by weight based on the total weight of the composition, since the particularly remarkable synergistic effect can be obtained. As stated before, the feature of the present invention is that the antibacterial and antifungal effects of dehydroacetic acid, sorbic acid or their alkali metal salts can be remarkably increased by the combination use with a slight amount of the component (B). Although the compounds employed as the component (B) are known as antibacterial and antifungal agents, it has now been found that synergistic antibacterial and antifungal effect unexpected from a single use of various known antibacterial and antifungal agents can be obtained, when among known antibacterial and antifungal agents the component (A) and the component (B) are particularly combined. When the content of the component (B) is less than 1% by weight, sufficient synergistic effect cannot be obtained. Also, even if the component (B) is employed in an amount of more than 40% by weight, the synergitic effect is not increased. Further, the compounds employed as the component (B) are relatively expensive and also the toxicity is higher than the component (A) and, therefore, the use of the component (B) in an amount of more than 40% by weight not only be uneconomical, but also may impair the low toxicity which is the feature of the composition of the present invention.

The adding amount of the composition varies depending on the kind of the products to be added. In general, sufficient antibacterial and antifungal effects can be obtained in an amount of 50 to 8,000 p.p.m.

Auxiliary agents such as other bactericides, other fungicides, surface active agents and perfumes may be incorporated in the composition of the invention, as occasion demands.

The composition of the present invention is applicable to any industrial products and agricultural products which require the annihilation or the prevention of propagation of bacteria and fungi, such as paints, sizing agents, petroleum products, plastic moldings, fibers, leathers, woods, paper goods, cosmetics, pharmacuticals, medical appliances, industrial equipments and building materials (putties, fiber boards, particle boards, gypsum boards), fruits, grains and vegetables.

The present invention is more particularly described and explained by means of the following Examples, in which all % are by weight unless otherwise noted.

EXAMPLE 1

A liquid culture medium of pH 7.0 containing 1% of peptone, 1% of meat extract and 0.1% of sodium chloride was prepared and sterilized, and 10 ml. portions thereof were poured into L-shaped tubes. After adding a prescribed amount of an antibacterial, antifungal composition consisting of the components (A) and (B) as shown in Table 1 to each tube, 0.1 ml. (number of cells: $5 \times 10^4$ cells/ml.) of an aqueous suspension of bacteria as shown in Table 1 was added to each tube. The thus prepared culture liquor contained $5 \times 10^2$ cells per milliliter. The culture was carried out at 37° C. for 48 hours with reciprocal shaking, and the state of the growth of bacteria was then observed by measuring the number of cells in 1 ml. of the culture liquor.

The results are shown in Table 1.

TABLE 1

| Bacteria | Antibacterial, antifungal composition | | (A)/(B) by weight | Amount of composition added (p.p.m.) | Number of cells (cells/ml.) |
| | Component (A) | Component (B) | | | |
| --- | --- | --- | --- | --- | --- |
| Staphylococcus aureus | Sodium dehydroacetate | N-(fluorodichloromethylthio)phthalimide | 95/5 | 500 | $25 \times 10$ |
| | | | 95/5 | 1000 | $3 \times 10$ |
| | | | 90/10 | 500 | $18 \times 10$ |
| | | | 90/10 | 1000 | 0 |
| | | | 80/20 | 500 | $17 \times 10$ |
| | | | 80/20 | 1000 | 0 |
| | | | 60/40 | 500 | 0 |
| | | | 100/0 | 500 | $19 \times 10^5$ |
| | | | 100/0 | 1000 | $18 \times 10^3$ |
| | | | 0/100 | 25 | $11 \times 10^8$ |
| | | | 0/100 | 50 | $10 \times 10^5$ |
| | | | 0/100 | 100 | $7 \times 10^4$ |
| | | | 0/100 | 200 | $6 \times 10^2$ |
| Staphylococcus aureus | Potassium sorbate | N-(fluorodichloromethylthio)phthalimide | 95/5 | 500 | $30 \times 10$ |
| | | | 95/5 | 1000 | 6 |
| | | | 90/10 | 500 | $22 \times 10$ |
| | | | 90/10 | 1000 | 0 |
| | | | 80/20 | 500 | $14 \times 10$ |
| | | | 80/20 | 1000 | 0 |
| | | | 60/40 | 500 | 0 |
| | | | 100/0 | 500 | $25 \times 10^7$ |
| | | | 100/0 | 1000 | $9 \times 10^5$ |
| | | | 0/100 | 25 | $11 \times 10^8$ |
| | | | 0/100 | 50 | $10 \times 10^5$ |
| | | | 0/100 | 100 | $7 \times 10^4$ |
| | | | 0/100 | 200 | $6 \times 10^2$ |
| Staphylococ- | Sorbic acid | N-(fluorodichloro- | | | |

TABLE 1-continued

| Bacteria | Antibacterial, antifungal composition | | (A)/(B) by weight | Amount of composition added (p.p.m.) | Number of cells (cells/ml.) |
| --- | --- | --- | --- | --- | --- |
| | Component (A) | Component (B) | | | |
| cus aureus | | methylthio)phthalimide | 95/5 | 500 | $25 \times 10$ |
| | | | 95/5 | 1000 | 0 |
| | | | 90/10 | 500 | $15 \times 10$ |
| | | | 90/10 | 1000 | 0 |
| | | | 80/20 | 500 | 0 |
| | | | 60/40 | 500 | 0 |
| | | | 100/0 | 500 | $21 \times 10^6$ |
| | | | 100/0 | 1000 | $5 \times 10^3$ |
| | | | 0/100 | 25 | $11 \times 10^8$ |
| | | | 0/100 | 50 | $10 \times 10^5$ |
| | | | 0/100 | 100 | $7 \times 10^4$ |
| | | | 0/100 | 200 | $6 \times 10^2$ |
| Bacillus Subtilis | Sodium dehydroacetate | Sodium o-phenylphenolate | | | |
| | | | 95/5 | 500 | $9 \times 10$ |
| | | | 95/5 | 1000 | 7 |
| | | | 90/10 | 500 | $8 \times 10$ |
| | | | 90/10 | 1000 | 0 |
| | | | 80/20 | 500 | $6 \times 10$ |
| | | | 80/20 | 1000 | 0 |
| | | | 60/40 | 500 | 0 |
| | | | 100/0 | 500 | $23 \times 10^7$ |
| | | | 100/0 | 1000 | $9 \times 10^4$ |
| | | | 0/100 | 25 | $3 \times 10^7$ |
| | | | 0/100 | 50 | $15 \times 10^4$ |
| | | | 0/100 | 100 | $6 \times 10^3$ |
| | | | 0/100 | 200 | $9 \times 10$ |
| Bacillus subtilis | Potassium sorbate | Sodium o-phenylphenolate | | | |
| | | | 95/5 | 500 | $15 \times 10$ |
| | | | 95/5 | 1000 | 2 |
| | | | 90/10 | 500 | $12 \times 10$ |
| | | | 90/10 | 1000 | 1 |
| | | | 80/20 | 500 | $6 \times 10$ |
| | | | 80/20 | 1000 | 0 |
| | | | 60/40 | 500 | 0 |
| | | | 100/0 | 500 | $7 \times 10^8$ |
| | | | 100/0 | 1000 | $5 \times 10^7$ |
| | | | 0/100 | 25 | $3 \times 10^7$ |
| | | | 0/100 | 50 | $15 \times 10^4$ |
| | | | 0/100 | 100 | $6 \times 10^3$ |
| | | | 0/100 | 200 | $9 \times 10$ |
| Bacillus subtilis | Sorbic acid | Sodium o-phenylphenolate | | | |
| | | | 95/5 | 500 | $15 \times 10$ |
| | | | 95/5 | 1000 | 0 |
| | | | 90/10 | 500 | $7 \times 10$ |
| | | | 90/10 | 1000 | 0 |
| | | | 80/20 | 500 | $3 \times 10$ |
| | | | 80/20 | 1000 | 0 |
| | | | 60/40 | 500 | 0 |
| | | | 100/0 | 500 | $13 \times 10^6$ |
| | | | 100/0 | 1000 | $18 \times 10^4$ |
| | | | 0/100 | 25 | $3 \times 10^7$ |
| | | | 0/100 | 50 | $15 \times 10^4$ |
| | | | 0/100 | 100 | $6 \times 10^3$ |
| | | | 0/100 | 200 | $9 \times 10$ |
| Staphylococcus aureus | Sodium dehydroacetate | 2-(4-Thiazolyl)-1H-benzimidazole | | | |
| | | | 95/5 | 500 | $21 \times 10$ |
| | | | 95/5 | 1000 | $6 \times 10$ |
| | | | 90/10 | 500 | $20 \times 10$ |
| | | | 90/10 | 1000 | 9 |
| | | | 80/20 | 500 | $19 \times 10$ |
| | | | 80/20 | 1000 | 8 |
| | | | 60/40 | 500 | $8 \times 10$ |
| | | | 60/40 | 1000 | 5 |
| | | | 100/0 | 500 | $19 \times 10^5$ |
| | | | 100/0 | 1000 | $18 \times 10^3$ |
| | | | 0/100 | 25 | $4 \times 10^9$ |
| | | | 0/100 | 50 | $4 \times 10^8$ |
| | | | 0/100 | 100 | $10 \times 10^6$ |
| | | | 0/100 | 200 | $5 \times 10^4$ |
| Staphylococcus aureus | Potassium sorbate | 2-(4-Thiazolyl)-1H-benzimidazole | | | |
| | | | 95/5 | 500 | $25 \times 10$ |
| | | | 95/5 | 1000 | $8 \times 10$ |
| | | | 90/10 | 500 | $24 \times 10$ |
| | | | 90/10 | 1000 | 15 |
| | | | 80/20 | 500 | $31 \times 10$ |
| | | | 80/20 | 1000 | 15 |
| | | | 60/40 | 500 | $29 \times 10$ |
| | | | 60/40 | 1000 | 10 |

TABLE 1-continued

| Bacteria | Antibacterial, antifungal composition | | (A)/(B) by weight | Amount of composition added (p.p.m.) | Number of cells (cells/ml.) |
| --- | --- | --- | --- | --- | --- |
| | Component (A) | Component (B) | | | |
| | | | 100/0 | 500 | $25 \times 10^7$ |
| | | | 100/0 | 1000 | $9 \times 10^5$ |
| | | | 0/100 | 25 | $4 \times 10^9$ |
| | | | 0/100 | 50 | $4 \times 10^8$ |
| | | | 0/100 | 100 | $10 \times 10^6$ |
| | | | 0/100 | 200 | $5 \times 10^4$ |
| Staphylococcus aureus | Sorbic acid | 2-(4-Thiazolyl)-1H-benzimidazole | | | |
| | | | 95/5 | 500 | $30 \times 10^2$ |
| | | | 95/5 | 1000 | $15 \times 10$ |
| | | | 90/10 | 500 | $41 \times 10$ |
| | | | 90/10 | 1000 | 35 |
| | | | 80/20 | 500 | $17 \times 10$ |
| | | | 80/20 | 1000 | 10 |
| | | | 60/40 | 500 | $6 \times 10$ |
| | | | 60/40 | 1000 | 5 |
| | | | 100/0 | 500 | $21 \times 10^6$ |
| | | | 100/0 | 1000 | $5 \times 10^3$ |
| | | | 0/100 | 25 | $4 \times 10^9$ |
| | | | 0/100 | 50 | $4 \times 10^8$ |
| | | | 0/100 | 100 | $10 \times 10^6$ |
| | | | 0/100 | 200 | $5 \times 10^4$ |
| Staphylococcus aureus | Sodium dehydroacetate | Methyl 1-(butylcarbamoyl)-2-benzimidazole-carbamate | | | |
| | | | 95/5 | 500 | $23 \times 10$ |
| | | | 95/5 | 1000 | 5 |
| | | | 90/10 | 500 | $21 \times 10$ |
| | | | 90/10 | 1000 | 0 |
| | | | 80/20 | 500 | $20 \times 10$ |
| | | | 80/20 | 1000 | 0 |
| | | | 60/40 | 500 | 0 |
| | | | 100/0 | 500 | $19 \times 10^5$ |
| | | | 100/0 | 1000 | $18 \times 10^3$ |
| | | | 0/100 | 25 | $7 \times 10^6$ |
| | | | 0/100 | 50 | $9 \times 10^4$ |
| | | | 0/100 | 100 | $12 \times 10^2$ |
| | | | 0/100 | 200 | $5 \times 10$ |
| Staphylococcus aureus | Potassium sorbate | Methyl 1-(butylcarbamoyl)-2-benzimidazole-carbamate | | | |
| | | | 95/5 | 500 | $32 \times 10$ |
| | | | 95/5 | 1000 | $10 \times 10$ |
| | | | 90/10 | 500 | $19 \times 10$ |
| | | | 90/10 | 1000 | 0 |
| | | | 80/20 | 500 | $28 \times 10$ |
| | | | 80/20 | 1000 | 0 |
| | | | 60/40 | 500 | 0 |
| | | | 100/0 | 500 | $25 \times 10^7$ |
| | | | 100/0 | 1000 | $9 \times 10^5$ |
| | | | 0/100 | 25 | $7 \times 10^6$ |
| | | | 0/100 | 50 | $9 \times 10^4$ |
| | | | 0/100 | 100 | $12 \times 10^2$ |
| | | | 0/100 | 200 | $5 \times 10$ |
| Staphylococcus aureus | Dehydroacetate | Methyl 1-(butylcarbamoyl)-2-benzimidazole-carbamate | | | |
| | | | 95/5 | 500 | $30 \times 10$ |
| | | | 90/5 | 1000 | $9 \times 10$ |
| | | | 90/10 | 500 | $15 \times 10$ |
| | | | 90/10 | 1000 | 0 |
| | | | 80/20 | 500 | $15 \times 10$ |
| | | | 80/20 | 1000 | 0 |
| | | | 60/40 | 500 | 0 |
| | | | 100/0 | 500 | $22 \times 10^5$ |
| | | | 100/0 | 1000 | $6 \times 10^3$ |
| | | | 0/100 | 25 | $7 \times 10^6$ |
| | | | 0/100 | 50 | $9 \times 10^4$ |
| | | | 0/100 | 100 | $12 \times 10^2$ |
| | | | 0/100 | 200 | $5 \times 10$ |
| Escherichia coli | Sodium dehydroacetate | Tetrachloroisophthalonitrile | | | |
| | | | 95/5 | 500 | 9 |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $7 \times 10^8$ |
| | | | 100/0 | 1000 | $9 \times 10^7$ |
| | | | 0/100 | 25 | $2 \times 10^5$ |
| | | | 0/100 | 50 | $9 \times 10^4$ |
| | | | 0/100 | 100 | $7 \times 10^2$ |
| | | | 0/100 | 200 | $3 \times 10$ |

TABLE 1-continued

| Bacteria | Antibacterial, antifungal composition | | (A)/(B) by weight | Amount of composition added (p.p.m.) | Number of cells (cells/ml.) |
| --- | --- | --- | --- | --- | --- |
| | Component (A) | Component (B) | | | |
| Escherichia coli | Potassium sorbate | Tetrachloroisophthalonitrile | 95/5 | 500 | 25 |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $6 \times 10^9$ |
| | | | 100/0 | 1000 | $12 \times 10^7$ |
| | | | 0/100 | 25 | $2 \times 10^5$ |
| | | | 0/100 | 50 | $9 \times 10^4$ |
| | | | 0/100 | 100 | $7 \times 10^2$ |
| | | | 0/100 | 200 | $3 \times 10$ |
| Escherichi coli | Dehydroacetic acid | Tetrachloroisophthalonitrile | 95/5 | 500 | 15 |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $13 \times 10^8$ |
| | | | 100/0 | 1000 | $31 \times 10^6$ |
| | | | 0/100 | 25 | $2 \times 10^5$ |
| | | | 0/100 | 50 | $9 \times 10^4$ |
| | | | 0/100 | 100 | $7 \times 10^2$ |
| | | | 0/100 | 200 | $3 \times 10$ |
| Pseudomonas aeruginosa | Sodium dehydroacetate | 8-Hydroxyquinoline sulfate | 95/5 | 500 | $9 \times 10$ |
| | | | 95/5 | 1000 | 0 |
| | | | 90/10 | 500 | $5 \times 10$ |
| | | | 90/10 | 1000 | 0 |
| | | | 80/20 | 500 | $8 \times 10$ |
| | | | 80/20 | 1000 | 0 |
| | | | 60/40 | 500 | $4 \times 10$ |
| | | | 60/40 | 1000 | 0 |
| | | | 100/0 | 500 | $15 \times 10^8$ |
| | | | 100/0 | 1000 | $2 \times 10^7$ |
| | | | 0/100 | 25 | $22 \times 10^6$ |
| | | | 0/100 | 50 | $21 \times 10^4$ |
| | | | 0/100 | 100 | $15 \times 10^2$ |
| | | | 0/100 | 200 | $4 \times 10$ |
| Pseudomonas aeruginosa | Potassium sorbate | 8-Hydroxyquinoline sulfate | 95/5 | 500 | $18 \times 10$ |
| | | | 95/5 | 1000 | 4 |
| | | | 90/10 | 500 | $16 \times 10$ |
| | | | 90/10 | 1000 | 0 |
| | | | 80/20 | 500 | $17 \times 10$ |
| | | | 80/20 | 1000 | 0 |
| | | | 60/40 | 500 | $16 \times 10$ |
| | | | 60/40 | 1000 | 0 |
| | | | 100/0 | 500 | $15 \times 10^{10}$ |
| | | | 100/0 | 1000 | $7 \times 10^8$ |
| | | | 0/100 | 25 | $22 \times 10^6$ |
| | | | 0/100 | 50 | $21 \times 10^4$ |
| | | | 0/100 | 100 | $15 \times 10^2$ |
| | | | 0/100 | 200 | $4 \times 10$ |
| Pseudomonas aeruginosa | Sorbic acid | 8-Hydroxyquinoline sulfate | 95/5 | 500 | $19 \times 10$ |
| | | | 95/5 | 1000 | 10 |
| | | | 90/10 | 500 | $21 \times 10$ |
| | | | 90/10 | 1000 | 8 |
| | | | 80/20 | 500 | $17 \times 10$ |
| | | | 80/20 | 1000 | 0 |
| | | | 60/40 | 500 | $14 \times 10$ |
| | | | 60/40 | 1000 | 0 |
| | | | 100/0 | 500 | $9 \times 10^9$ |
| | | | 100/0 | 1000 | $8 \times 10^7$ |
| | | | 0/100 | 25 | $22 \times 10^6$ |
| | | | 0/100 | 50 | $21 \times 10^4$ |
| | | | 0/100 | 100 | $15 \times 10^2$ |
| | | | 0/100 | 200 | $4 \times 10$ |
| Pseudomonas aeruginosa | Sodium dehydroacetate | p-Chloro-m-xylenol | 95/5 | 500 | $15 \times 10$ |
| | | | 95/5 | 1000 | 0 |
| | | | 90/10 | 500 | $13 \times 10$ |
| | | | 90/10 | 1000 | 0 |
| | | | 80/20 | 500 | $12 \times 10$ |
| | | | 80/20 | 1000 | 0 |
| | | | 60/40 | 500 | 0 |
| | | | 100/0 | 500 | $15 \times 10^8$ |

TABLE 1-continued

| Bacteria | Antibacterial, antifungal composition Component (A) | Component (B) | (A)/(B) by weight | Amount of composition added (p.p.m.) | Number of cells (cells/ml.) |
|---|---|---|---|---|---|
| | | | 100/0 | 1000 | $2 \times 10^7$ |
| | | | 0/100 | 25 | $8 \times 10^9$ |
| | | | 0/100 | 50 | $15 \times 10^6$ |
| | | | 0/100 | 100 | $18 \times 10^4$ |
| | | | 0/100 | 200 | $13 \times 10^2$ |
| *Pseudomonas aeruginosa* | Potassium sorbate | p-Chloro-m-xylenol | | | |
| | | | 95/5 | 500 | $20 \times 10$ |
| | | | 95/5 | 1000 | 7 |
| | | | 90/10 | 500 | $17 \times 10$ |
| | | | 90/10 | 1000 | 5 |
| | | | 80/20 | 500 | $15 \times 10$ |
| | | | 80/20 | 1000 | 5 |
| | | | 60/40 | 500 | $3 \times 10$ |
| | | | 60/40 | 1000 | 0 |
| | | | 100/0 | 500 | $15 \times 10^{10}$ |
| | | | 100/0 | 1000 | $7 \times 10^8$ |
| | | | 0/100 | 25 | $8 \times 10^9$ |
| | | | 0/100 | 50 | $15 \times 10^6$ |
| | | | 0/100 | 100 | $18 \times 10^4$ |
| | | | 0/100 | 200 | $13 \times 10^2$ |
| *Pseudomonas aeruginosa* | Sorbic acid | p-Chloro-m-xylenol | | | |
| | | | 95/5 | 500 | $18 \times 10$ |
| | | | 95/5 | 1000 | 5 |
| | | | 90/10 | 500 | $10 \times 10$ |
| | | | 90/10 | 1000 | 0 |
| | | | 80/20 | 500 | $9 \times 10$ |
| | | | 80/20 | 1000 | 0 |
| | | | 60/40 | 500 | 0 |
| | | | 100/0 | 500 | $9 \times 10^9$ |
| | | | 100/0 | 1000 | $8 \times 10^7$ |
| | | | 0/100 | 25 | $8 \times 10^9$ |
| | | | 0/100 | 50 | $15 \times 10^6$ |
| | | | 0/100 | 100 | $18 \times 10^4$ |
| | | | 0/100 | 200 | $13 \times 10^2$ |

EXAMPLE 2

A 5% aqueous solution of starch was prepared and sterilized, and 100 ml. portions thereof were poured into 200 ml. bottles. After adding a prescribed amount of an antibacterial, antifungal composition consisting of the components (A) and (B) as shown in Table 2 to each bottle and thoroughly agitating, 1 ml. (number of fungi: $5 \times 10^6$ fungi/ml.) of an aqueous suspension of fungi as shown in Table 2 was added to each bottle and was agitated again. The thus prepared aqueous solution contained $5 \times 10^4$ fungi per gram. The bottles were then sealed and allowed to stand at 30° C. for a week. The state of the growth of fungi was observed by measuring the number of fungi in 1 g. of the aqueous solution.

The results are shown in Table 2.

TABLE 2

| Fungi | Antibacterial, antifungal composition Component (A) | Component (B) | (A)/(B) by weight | Amount of composition added (p.p.m.) | Number of fungi (fungi/g.) |
|---|---|---|---|---|---|
| *Trichoderma viride* | Sodium dehydroacetate | N-(fluorodichloro-methylthio)phthalimide | 95/5 | 100 | $4 \times 10$ |
| | | | 95/5 | 500 | 0 |
| | | | 90/10 | 100 | $2 \times 10$ |
| | | | 90/10 | 500 | 0 |
| | | | 80/20 | 100 | 8 |
| | | | 80/20 | 500 | 0 |
| | | | 60/40 | 100 | 0 |
| | | | 100/0 | 100 | $29 \times 10^8$ |
| | | | 100/0 | 500 | $34 \times 10^5$ |
| | | | 0/100 | 5 | $7 \times 10^7$ |
| | | | 0/100 | 25 | $16 \times 10^6$ |
| | | | 0/100 | 50 | $33 \times 10^4$ |
| | | | 0/100 | 100 | $5 \times 10^2$ |
| *Trichoderma viride* | Potassium sorbate | N-(fluorodichloro-methylthio)phthalimide | 95/5 | 100 | $8 \times 10$ |
| | | | 95/5 | 500 | 0 |
| | | | 90/10 | 100 | $5 \times 10$ |
| | | | 90/10 | 500 | 0 |
| | | | 80/20 | 100 | 7 |
| | | | 80/20 | | |
| | | | 60/40 | 100 | 0 |
| | | | 100/0 | 100 | $27 \times 10^{10}$ |
| | | | 100/0 | 500 | $9 \times 10^8$ |
| | | | 0/100 | 5 | $7 \times 10^7$ |

TABLE 2-continued

| Fungi | Antibacterial, antifungal composition | | (A)/(B) by weight | Amount of composition added (p.p.m.) | Number of fungi (fungi/g.) |
|---|---|---|---|---|---|
| | Component (A) | Component (B) | | | |
| | | | 0/100 | 25 | $16 \times 10^6$ |
| | | | 0/100 | 50 | $33 \times 10^4$ |
| | | | 0/100 | 100 | $5 \times 10^2$ |
| Trichoderma viride | Dehydroacetic acid | N-(fluorodichloromethylthio)phthalimide | 95/5 | 100 | $3 \times 10$ |
| | | | 95/5 | 500 | 0 |
| | | | 90/10 | 100 | 0 |
| | | | 80/20 | 100 | 0 |
| | | | 60/40 | 100 | 0 |
| | | | 100/0 | 100 | $25 \times 10^8$ |
| | | | 100/0 | 500 | $30 \times 10^5$ |
| | | | 0/100 | 5 | $7 \times 10^7$ |
| | | | 0/100 | 25 | $16 \times 10^6$ |
| | | | 0/100 | 50 | $33 \times 10^4$ |
| | | | 0/100 | 100 | $5 \times 10^2$ |
| Cladosporium resinae | Sodium dehydroacetate | Sodium o-phenylphenolate | 95/5 | 500 | $8 \times 10$ |
| | | | 95/5 | 1000 | 5 |
| | | | 90/10 | 500 | 5 |
| | | | 90/10 | 1000 | 0 |
| | | | 80/20 | 500 | 5 |
| | | | 80/20 | 1000 | 0 |
| | | | 60/40 | 500 | 0 |
| | | | 100/0 | 500 | $31 \times 10^6$ |
| | | | 100/0 | 1000 | $28 \times 10^3$ |
| | | | 0/100 | 25 | $8 \times 10^{10}$ |
| | | | 0/100 | 50 | $18 \times 10^8$ |
| | | | 0/100 | 100 | $34 \times 10^6$ |
| | | | 0/100 | 200 | $5 \times 10$ |
| Cladosporium resinae | Potassium sorbate | Sodium o-phenylphenolate | 95/5 | 500 | $15 \times 10$ |
| | | | 95/5 | 1000 | 3 |
| | | | 90/10 | 500 | $10 \times 10$ |
| | | | 90/10 | 1000 | 0 |
| | | | 80/20 | 500 | 9 |
| | | | 80/20 | 1000 | 0 |
| | | | 60/40 | 500 | 0 |
| | | | 100/0 | 500 | $13 \times 10^6$ |
| | | | 100/0 | 1000 | $25 \times 10^3$ |
| | | | 0/100 | 25 | $8 \times 10^{10}$ |
| | | | 0/100 | 50 | $18 \times 10^8$ |
| | | | 0/100 | 100 | $34 \times 10^6$ |
| | | | 0/100 | 200 | $5 \times 10$ |
| Cladosporium resinae | Dehydroacetic acid | Sodium o-phenylphenolate | 95/5 | 500 | $7 \times 10$ |
| | | | 95/5 | 1000 | 0 |
| | | | 90/10 | 500 | 4 |
| | | | 90/10 | 1000 | 0 |
| | | | 80/20 | 500 | 0 |
| | | | 60/40 | 500 | 0 |
| | | | 100/0 | 500 | $10 \times 10^5$ |
| | | | 100/0 | 1000 | $9 \times 10^3$ |
| | | | 0/100 | 25 | $8 \times 10^{10}$ |
| | | | 0/100 | 50 | $18 \times 10^8$ |
| | | | 0/100 | 100 | $34 \times 10^6$ |
| | | | 0/100 | 200 | $5 \times 10$ |
| Aspergillus niger | Sodium dehydroacetate | 2-(4-Thiazolyl)-1H-benzimidazole | 95/5 | 500 | $7 \times 10$ |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $18 \times 10^{10}$ |
| | | | 100/0 | 1000 | $30 \times 10^4$ |
| | | | 0/100 | 25 | $37 \times 10^8$ |
| | | | 0/100 | 50 | $18 \times 10^5$ |
| | | | 0/100 | 100 | $11 \times 10^3$ |
| | | | 0/100 | 200 | $4 \times 10$ |
| Aspergillus niger | Potassium sorbate | 2-(4-Thiazolyl)-1H-benzimidazole | 95/5 | 500 | $21 \times 10$ |
| | | | 95/5 | 1000 | 3 |
| | | | 90/10 | 500 | $3 \times 10$ |
| | | | 90/10 | 1000 | 0 |
| | | | 80/20 | 500 | 0 |
| | | | 60/40 | 500 | 0 |
| | | | 100/0 | 500 | $7 \times 10^{10}$ |
| | | | 100/0 | 1000 | $37 \times 10^8$ |
| | | | 0/100 | 25 | $37 \times 10^8$ |

TABLE 2-continued

| Fungi | Antibacterial, antifungal composition Component (A) | Component (B) | (A)/(B) by weight | Amount of composition added (p.p.m.) | Number of fungi (fungi/g.) |
|---|---|---|---|---|---|
| | | | 0/100 | 50 | $18 \times 10^5$ |
| | | | 0/100 | 100 | $11 \times 10^3$ |
| | | | 0/100 | 200 | $4 \times 10$ |
| Aspergillus niger | Dehydroacetic acid | 2-(4-Thiazolyl)-1H-benzimidazole | 95/5 | 500 | $5 \times 10$ |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $17 \times 10^{10}$ |
| | | benzimidazole | 100/0 | 1000 | $25 \times 10^4$ |
| | | | 0/100 | 25 | $37 \times 10^8$ |
| | | | 0/100 | 50 | $18 \times 10^5$ |
| | | | 0/100 | 100 | $11 \times 10^3$ |
| | | | 0/100 | 200 | $4 \times 10$ |
| Penicillium citrinum | Sodium dehydroacetate | Methyl 1-(butylcarbamoyl)-2-benzimidazole-carbamate | 95/5 | 500 | $23 \times 10$ |
| | | | 95/5 | 1000 | 8 |
| | | | 90/10 | 500 | $2 \times 10$ |
| | | | 90/10 | 1000 | 0 |
| | | | 80/20 | 5000 | 5 |
| | | | 80/20 | 1000 | 0 |
| | | | 60/40 | 500 | 0 |
| | | | 100/0 | 500 | $17 \times 10^5$ |
| | | | 100/0 | 1000 | $35 \times 10^4$ |
| | | | 0/100 | 25 | $13 \times 10^8$ |
| | | | 0/100 | 50 | $19 \times 10^6$ |
| | | | 0/100 | 100 | $9 \times 10^3$ |
| | | | 0/100 | 200 | $3 \times 10$ |
| Penicillium citrinum | Potassium sorbate | Methyl 1-(butylcarbamoyl)-2-benzimidazole-carbamate | 95/5 | 500 | $19 \times 10$ |
| | | | 95/5 | 1000 | 9 |
| | | | 90/10 | 500 | $10 \times 10$ |
| | | | 90/10 | 1000 | 1 |
| | | | 80/20 | 500 | 7 |
| | | | 80/20 | 1000 | 0 |
| | | | 60/40 | 500 | 0 |
| | | | 100/0 | 500 | $4 \times 10^9$ |
| | | | 100/0 | 1000 | $12 \times 10^7$ |
| | | | 0/100 | 25 | $13 \times 10^8$ |
| | | | 0/100 | 50 | $19 \times 10^6$ |
| | | | 0/100 | 100 | $9 \times 10^3$ |
| | | | 0/100 | 200 | $3 \times 10$ |
| Penicillium citrinum | Sorbic acid | Methyl 1-(butylcarbamoyl)-2-benzimidazole-carbamate | 95/5 | 500 | $8 \times 10$ |
| | | | 95/5 | 1000 | 5 |
| | | | 90/10 | 500 | $5 \times 10$ |
| | | | 90/10 | 1000 | 2 |
| | | | 80/20 | 500 | 0 |
| | | | 60/40 | 500 | 0 |
| | | | 100/0 | 500 | $7 \times 10^7$ |
| | | | 100/0 | 1000 | $40 \times 10^5$ |
| | | | 0/100 | 25 | $13 \times 10^8$ |
| | | | 0/100 | 50 | $19 \times 10^6$ |
| | | | 0/100 | 100 | $9 \times 10^3$ |
| | | | 0/100 | 200 | $3 \times 10$ |
| Aspergillus niger | Sodium dehydroacetate | Tetrachloroisophthalonitrile | 95/5 | 100 | 2 |
| | | | 95/5 | 500 | 0 |
| | | | 90/10 | 100 | 0 |
| | | | 80/20 | 100 | 0 |
| | | | 60/40 | 100 | 0 |
| | | | 100/0 | 100 | $25 \times 10^{10}$ |
| | | | 100/0 | 500 | $18 \times 10^7$ |
| | | | 0/100 | 5 | $7 \times 10^4$ |
| | | | 0/100 | 25 | $8 \times 10^3$ |
| | | | 0/100 | 50 | $3 \times 10$ |
| Aspergillus niger | Potassium sorbate | Tetrachloroisophthalonitrile | 95/5 | 100 | $13 \times 10$ |
| | | | 95/5 | 500 | 0 |
| | | | 90/10 | 100 | 0 |
| | | | 80/20 | 100 | 0 |
| | | | 60/40 | 100 | 0 |
| | | | 100/0 | 100 | $33 \times 10^{11}$ |
| | | | 100/0 | 500 | $7 \times 10^{10}$ |
| | | | 0/100 | 5 | $7 \times 10^4$ |
| | | | 0/100 | 25 | $8 \times 10^3$ |
| | | | 0/100 | 50 | $3 \times 10$ |

TABLE 2-continued

| Fungi | Antibacterial, antifungal composition Component (A) | Component (B) | (A)/(B) by weight | Amount of composition added (p.p.m.) | Number of fungi (fungi/g.) |
|---|---|---|---|---|---|
| Aspergillus niger | Sorbic acid | Tetrachloroisophthalo-nitrile | 95/5 | 100 | $10 \times 10$ |
| | | | 95/5 | 500 | 0 |
| | | | 90/10 | 100 | 0 |
| | | | 80/20 | 100 | 0 |
| | | | 60/40 | 100 | 0 |
| | | | 100/0 | 100 | $32 \times 10^{10}$ |
| | | | 100/0 | 500 | $5 \times 10^9$ |
| | | | 0/100 | 5 | $7 \times 10^4$ |
| | | | 0/100 | 25 | $8 \times 10^3$ |
| | | | 0/100 | 50 | $3 \times 10$ |
| Aspergillus niger | Sodium dehydroacetate | 8-Hydroxyquinoline sulfate | 95/5 | 500 | 3 |
| | | | 95/5 | 1000 | 0 |
| | | | 90/10 | 500 | 2 |
| | | | 90/10 | 1000 | 0 |
| | | | 80/20 | 500 | 0 |
| | | | 60/40 | 500 | 0 |
| | | | 100/0 | 500 | $18 \times 10^7$ |
| | | | 100/0 | 1000 | $30 \times 10^4$ |
| | | | 0/100 | 25 | $10 \times 10^6$ |
| | | | 0/100 | 50 | $7 \times 10^3$ |
| | | | 0/100 | 100 | $6 \times 10^2$ |
| | | | 0/100 | 200 | $6 \times 10$ |
| Aspergillus niger | Potassium sorbate | 8-Hydroxyquinoline sulfate | 95/5 | 500 | $13 \times 10$ |
| | | | 95/5 | 1000 | 0 |
| | | | 90/10 | 500 | 8 |
| | | | 90/10 | 1000 | 0 |
| | | | 80/20 | 500 | 0 |
| | | | 60/40 | 500 | 0 |
| | | | 100/0 | 500 | $7 \times 10^{10}$ |
| | | | 100/0 | 1000 | $37 \times 10^8$ |
| | | | 0/100 | 25 | $10 \times 10^6$ |
| | | | 0/100 | 50 | $7 \times 10^3$ |
| | | | 0/100 | 100 | $6 \times 10^2$ |
| | | | 0/100 | 200 | $6 \times 10$ |
| Aspergillus niger | Dehydroacetic acid | 8-Hydroxyquinoline sulfate | 95/5 | 500 | 2 |
| | | | 95/5 | 1000 | 0 |
| | | | 90/10 | 500 | 2 |
| | | | 90/10 | 1000 | 0 |
| | | | 80/20 | 500 | 0 |
| | | | 60/40 | 500 | 0 |
| | | | 100/0 | 500 | $10 \times 10^7$ |
| | | | 100/0 | 1000 | $25 \times 10^4$ |
| | | | 0/100 | 25 | $10 \times 10^6$ |
| | | | 0/100 | 50 | $7 \times 10^3$ |
| | | | 0/100 | 100 | $6 \times 10^2$ |
| | | | 0/100 | 200 | $6 \times 10$ |
| Aspergillus niger | Sodium dehydroacetate | p-Chloro-m-xylenol | 95/5 | 500 | $10 \times 10$ |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $18 \times 10^7$ |
| | | | 100/0 | 1000 | $30 \times 10^4$ |
| | | | 0/100 | 25 | $14 \times 10^9$ |
| | | | 0/100 | 50 | $16 \times 10^6$ |
| | | | 0/100 | 100 | $12 \times 10^4$ |
| | | | 0/100 | 200 | $5 \times 10$ |
| Aspergillus niger | Potassium sorbate | p-Chloro-m-xylenol | 95/5 | 500 | $15 \times 10$ |
| | | | 95/5 | 1000 | 0 |
| | | | 90/10 | 500 | $5 \times 10$ |
| | | | 90/10 | 1000 | 0 |
| | | | 80/20 | 500 | 0 |
| | | | 60/40 | 500 | 0 |
| | | | 100/0 | 500 | $7 \times 10^{10}$ |
| | | | 100/0 | 1000 | $37 \times 10^8$ |
| | | | 0/100 | 25 | $14 \times 10^9$ |
| | | | 0/100 | 50 | $16 \times 10^6$ |
| | | | 0/100 | 100 | $12 \times 10^4$ |
| | | | 0/100 | 200 | $5 \times 10$ |
| Aspergillus niger | Dehydroacetic acid | p-Chloro-m-xylenol | 95/5 | 500 | $6 \times 10$ |
| | | | 95/5 | 1000 | 0 |

TABLE 2-continued

| Fungi | Antibacterial, antifungal composition | | (A)/(B) by weight | Amount of composition added (p.p.m.) | Number of fungi (fungi/g.) |
|---|---|---|---|---|---|
| | Component (A) | Component (B) | | | |
| | | | 90/10 | 500 | 0 |
| | | | 80/20 | 500 | 0 |
| | | | 60/40 | 500 | 0 |
| | | | 100/0 | 500 | $10 \times 10^7$ |
| | | | 100/0 | 1000 | $25 \times 10^4$ |
| | | | 0/100 | 25 | $14 \times 10^9$ |
| | | | 0/100 | 50 | $16 \times 10^6$ |
| | | | 0/100 | 100 | $12 \times 10^4$ |
| | | | 0/100 | 200 | $5 \times 10$ |

EXAMPLE 3

A 2% of aqueous solution of carboxymethyl cellulose was prepared and adjusted to pH 7. After adding an antibacterial, antifungal composition consisting of the components (A) and (B) to the solution in a concentration as shown in Table 3, a slight amount of a putrid carboxymethyl cellulose was added to the solution. The solution was stored in an air-conditioned room at 37° C. and the putrefaction of the solution was obserbed with the lapse of time.

The results are shown in Table 3, in which symbols are as follows:

—: No putrefaction
+: Putrefaction

TABLE 3

| Antibacterial, antifungal composition | | | | Time elapsed | | |
|---|---|---|---|---|---|---|
| Component (A) | Concentration (p.p.m.) | Component (B) | Concentration (p.p.m.) | After 1 week | After 2 weeks | After 3 weeks |
| Sodium dehydroacetate | 500 | Sodium o-phenylphenolate | 10 | — | — | — |
| Potassium sorbate | 500 | Sodium o-phenylphenolate | 50 | — | — | — |
| — | 0 | Sodium o-phenylphenolate | 100 | — | + | + |
| Sodium dehydroacetate | 2000 | — | 0 | — | — | + |
| Potassium sorbate | 2000 | — | 0 | — | + | + |
| — | 0 | — | 0 | + | + | + |

EXAMPLE 4

An antibacterial, antifungal composition was added to a 6% aqueous solution of glue in a concentration as shown in Table 4. The solution was stored in an air-conditioned room at 50° C. and the decrease of the viscosity due to putrefaction was observed with the lapse of time.

The results are shown in Table 4, in which symbols are as follows:

—: No decrease of viscosity
+: Decrease of viscosity

TABLE 4

| Antibacterial, antifungal composition | | | | Time elapsed | | |
|---|---|---|---|---|---|---|
| Component (A) | Concentration (p.p.m.) | Component (B) | Concentration (p.p.m.) | After 1 week | After 2 weeks | After 3 weeks |
| Sodium dehydroacetate | 1000 | Sodium o-phenylphenolate | 50 | — | — | — |
| Potassium sorbate | 2000 | Sodium o-phenylphenolate | 50 | — | — | — |
| — | 0 | Sodium o-pehnylphenolate | 200 | + | + | + |
| Sodium dehydroacetate | 5000 | — | 0 | — | — | + |
| Potassium sorbate | 5000 | — | 0 | — | — | + |
| — | 0 | — | 0 | + | + | + |

EXAMPLE 5

An antibacterial, antifungal composition was added to an ethylene-vinyl acetate copolymer emulsion containing polyvinyl alcohol as an emulsifier in a concentration as shown in Table 5. A slight amount of a putrid emulsion was added to the emulsion and the number of cells was immediately measured. The emulsion was then stored in an air-conditioned room at 30° C., and after 3 weeks, the number of cells in the emulsion was measured again to determine the preservative and fungicidal effects.

The results are shown in Table 5.

TABLE 5

| Antibacterial, antifungal composition | | | | Number of cells (cell/g.) | | | | | |
|---|---|---|---|---|---|---|---|---|---|
| | Concentration | | Concentration | Before storage | | | After 3 weeks | | |
| Component (A) | (p.p.m.) | Component (B) | (p.p.m.) | Fungi | Yeast | Bacteria | Fungi | Yeast | Bacteria |
| Potassium dehydroacetate | 3000 | Sodium o-phenylphenolate | 100 | $51 \times 10^6$ | $15 \times 10^6$ | $7 \times 10^3$ | $<10^2$ | $<10^2$ | $2 \times 10^2$ |
| Potassium sorbate | 4000 | Sodium o-phenylphenolate | 200 | $35 \times 10^6$ | $19 \times 10^6$ | $5 \times 10^3$ | $<10^2$ | $<10^2$ | $4 \times 10^2$ |
| Potassium | 0 | Sodium o-phe- | 1000 | $25 \times 10^6$ | $19 \times 10^6$ | $9 \times 10^3$ | $31 \times 10^5$ | $22 \times 10^5$ | $9 \times 10^3$ |

TABLE 5-continued

| Antibacterial, antifungal composition | | | | Number of cells (cell/g.) | | | | | |
|---|---|---|---|---|---|---|---|---|---|
| | Concentration | | Concentration | Before storage | | | After 3 weeks | | |
| Component (A) | (p.p.m.) | Component (B) | (p.p.m.) | Fungi | Yeast | Bacteria | Fungi | Yeast | Bacteria |
| sorbate Sodium dehydroacetate | 5000 | nylphenolate Sodium o-phenylphenolate | 0 | $30 \times 10^6$ | $26 \times 10^6$ | $6 \times 10^3$ | $72 \times 10^4$ | $18 \times 10^4$ | $6 \times 10^3$ |
| Potassium sorbate | 5000 | Sodium o-phenylphenolate | 0 | $17 \times 10^6$ | $24 \times 10^6$ | $6 \times 10^3$ | $10 \times 10^6$ | $29 \times 10^5$ | $5 \times 10^3$ |
| Potassium sorbate | 0 | Sodium o-phenylphenolate | 0 | $51 \times 10^6$ | $18 \times 10^6$ | $8 \times 10^3$ | $23 \times 10^7$ | $25 \times 10^6$ | $8 \times 10^3$ |

EXAMPLE 6

A 10% aqueous solution of a polyvinyl alcohol sizing agent was prepared and divided into three portions. To the first portion was added no medicine, to the second portion was added 2,000 p.p.m. of sodium dehydroacetate, and to the third portion were added 1,000 p.p.m. of sodium dehydroacetate and 100 p.p.m. of p-chloro-m-xylenol. Epicoccum sp. was inoculated to each of the three portions, and they were placed in an incubator at 30° C. and allowed to stand for 14 days.

In the first and second portions, development of fungi was observed after 3 and 5 days, respectively, but in the third position no development of fungi was observed.

The above procedure was repeated except that, as the component (B), 2-(4-thiazolyl)-1H-benzimidazole, 8-hydroxyquinoline sulfate, methyl 1-(butylcarbamoyl)-2-benzimidazolecarbamate, tetrachloroisophthalonitrile or N-(fluorodichloromethylthio)phthalimide was employed instead of p-chloro-m-xylenol. The same results as above were obtained with respect to all the above compounds.

EXAMPLE 7

The procedures of Example 6 were repeated except that potassium sorbate was employed instead of sodium dehydroacetate.

With respect to all tests using six components (B) in Example 6, in the first and second portions development of fungi was observed after 4 and 6 days, respectively, but in the third portion no development of fungi was observed.

EXAMPLE 8

An antibacterial, antifungal composition was prepared by admixing 95 g. of sodium dehydroacetate as the component (A) and 5 g. of the component (B) shown in Table 6. The composition was added to a 18% solution of a crotonic acid-vinyl acetate copolymer in a concentration of 2,500 p.p.m., 5,000 p.p.m. or 7,500 p.p.m. to give three kinds of the coating solutions.

Each solution was sprayed onto two sides of a fancy mat (10×10 cm.) in an amount of 2 g. on each side, and was then dried at 140° C. for 2 minutes.

The coated fancy mats were allowed to stand under a saturated humidity at 25° C., and the state of the growth of fungi was observed with the lapse of time.

The results are shown in Table 6, in which symbols are as follows:

- −: No growth
- ±: A little growth
- +: Growth (The more the number of the symbol +, the larger the growth.)

TABLE 6

| Component (B) | Concentration of composition (p.p.m.) | Days elapsed | | | | | | |
|---|---|---|---|---|---|---|---|---|
| | | 5 | 6 | 7 | 8 | 10 | 12 | 14 |
| p-Chloro-m-xylenol | 0 | − | − | + | ++ | +++ | +++++ | +++++ |
| | 2500 | − | − | ± | + | +++ | +++ | ++++ |
| | 5000 | − | − | − | ± | + | ++ | +++ |
| | 7500 | − | − | − | − | − | − | − |
| 2-(4-Thiazolyl)-1H-benzimidazole | 0 | − | + | ++ | +++ | ++++ | +++++ | +++++ |
| | 2500 | − | − | + | + | +++ | +++ | ++++ |
| | 5000 | − | − | − | ± | + | ++ | +++ |
| | 7500 | − | − | − | − | − | − | − |
| 8-Hydroxyquinoline sulfate | 0 | − | + | ++ | +++ | ++++ | +++++ | +++++ |
| | 2500 | − | − | + | + | +++ | +++ | ++++ |
| | 5000 | − | − | − | ± | + | ++ | +++ |
| | 7500 | − | − | − | − | − | − | − |
| Methyl 1-(butylcarbamoyl)-2-benzimidazolecarbamate | 0 | − | + | ++ | +++ | ++++ | +++++ | +++++ |
| | 2500 | − | − | + | + | +++ | +++ | ++++ |
| | 5000 | − | − | − | ± | + | ++ | +++ |
| | 7500 | − | − | − | − | − | − | − |
| Tetrachloroisophthalonitrile | 0 | − | + | ++ | +++ | ++++ | +++++ | +++++ |
| | 2500 | − | − | ± | + | +++ | +++ | ++++ |
| | 5000 | − | − | − | − | ± | + | + |
| | 7500 | − | − | − | − | − | − | − |
| N-(fluorodichloromethylthio)-phthalimide | 0 | − | + | ++ | +++ | ++++ | +++++ | +++++ |
| | 2500 | − | ± | + | + | +++ | +++ | ++++ |
| | 5000 | − | − | − | ± | + | ++ | +++ |
| | 7500 | − | − | − | − | − | − | − |

EXAMPLE 9

A sizing solution containing 5% of wheat starch and a sizing solution containing 5% a casein were prepared, and thereto was added an antibacterial or antifungal agent as shown in Table 7. After adding a suspension of fungi consisting of *Aspergillus niger, Penicillium citrinum, Cladosporium herbaum* and *Chaetomium globosum* to each of the sizing solutions, the sizing solutions were placed in an incubator at 28° C. and the state of the growth of fungi was observed with the lapse of time.

The results are shown in Table 7, in which symbols are as follows:

−: No growth
±: A little growth
+: Growth (The more the number of the symbol +, the larger the growth.)

TABLE 7

| Sizing solution | Antibacterial, antifungal agent | Incubation days | | | | | |
|---|---|---|---|---|---|---|---|
| | | 0 | 4 | 7 | 14 | 21 | 28 |
| Wheat starch | None | − | +++ | ++++ | ++++ | ++++ | ++++ |
| Casein | None | − | − | ++ | +++ | ++++ | ++++ |
| Wheat Starch | Sodium dehydroacetate (500 p.p.m.) | − | − | ± | ++ | +++ | +++ |
| Casein | Sodium dehydroacetate (500 p.p.m.) | − | − | − | + | ++ | +++ |
| Wheat starch | Sodium dehydroacetate (475 p.p.m.) and p-Chloro-m-xylenol (25 p.p.m.) | − | − | − | − | − | − |
| Casein | Sodium dehydroacetate (475 p.p.m.) and p-Chloro-m-xylenol (25 p.p.m.) | − | − | − | − | − | − |
| Wheat starch | Sodium dehydroacetate (475 p.p.m.) and 2-(4-Thiazolyl)-1H-benzimidazole (25 p.p.m.) | − | − | − | − | − | − |
| Casein | Sodium dehydroacetate (475 p.p.m.) and 2-(4-Thiazoly-1H-benzimidazol 25 p.p.m.) | − | − | − | − | − | − |
| Wheat starch | Sodium dehydroacetate (475 p.p.m.) and 8-Hydroxyquinoline sulfate (25 p.p.m.) | − | − | − | − | − | − |
| Casein | Sodium dehydroacetate (475 p.p.m.) and 8-Hydroxyquinoline sulfate (25 p.p.m.) | − | − | − | − | − | − |
| Wheat starch | Sodium dehydroacetate (475 p.p.m.) and Methyl 1-(butylcarbamoyl)-2-benzimidazole carbamate (25 p.p.m.) | − | − | − | − | − | − |
| Casein | Sodium dehydroacetate (475 p.p.m. and Methyl 1-(butylcarbamoyl)-2-benzimidazolecarbamate (25 p.p.m.) | − | − | − | − | − | − |
| Wheat starch | Sodium dehydroacetate (475 p.p.m.) and Tetrachloroisophthalonitrile 25 p.p.m. and Sodium dehydroacetate (475 p.p.m.) and | − | − | − | − | − | − |
| Casein | Sodium dehydroacetate (475 p.p.m.) and − | − | − | − | − | − | − |
| Wheat Starch | Sodium dehydroacetate (475 p.p.m.) and N-(fluorodichloromethylthio)phthalimide (25 p.p.m.) | − | − | − | − | − | − |
| Casein | Sodium dehydroacetate (475 p.p.m.) and N-(fluorodichloromethylthio)phthalamide (25 p.p.m.) | − | − | − | − | − | − |

What we claim is:

1. An antibacterial and antifungal composition comprising a mixture of:
   (A) at least one member selected from the group consisting of sorbic acid, and its alkali metal salts; and (B) 2-(4-thiazolyl)-1H-Benzimidazole, wherein the weight ratio of component (A) to component (B) is in the range of 95/5 to 60/40.

* * * * *